United States Patent [19]

Waldbillig et al.

[11] Patent Number: 4,743,235
[45] Date of Patent: May 10, 1988

[54] FLUSH CONTROL DEVICE

[75] Inventors: Charles C. Waldbillig, Columbus; Jon F. Short, London, both of Ohio

[73] Assignee: Medex, Inc., Hilliard, Ohio

[21] Appl. No.: 903,730

[22] Filed: Sep. 5, 1986

[51] Int. Cl.⁴ ............................................. A61M 5/00
[52] U.S. Cl. ....................................... 604/250; 604/246
[58] Field of Search ................... 604/250, 30, 34, 246

[56] References Cited

U.S. PATENT DOCUMENTS

| | | |
|---|---|---|
| 3,675,891 | 7/1972 | Reynolds et al. |
| 4,192,303 | 3/1980 | Young et al. |
| 4,245,636 | 1/1981 | Sparks et al. |
| 4,267,833 | 5/1981 | Barger et al. |
| 4,267,834 | 5/1981 | Barger et al. |
| 4,267,835 | 5/1981 | Barger et al. |
| 4,278,083 | 7/1981 | Young et al. |
| 4,337,770 | 7/1982 | Young et al. |
| 4,381,591 | 5/1983 | Barger et al. |
| 4,464,179 | 8/1984 | Barger et al. |

*Primary Examiner*—C. Fred Rosenbaum
*Assistant Examiner*—Gene B. Kartchner
*Attorney, Agent, or Firm*—Wood, Herron & Evans

[57] ABSTRACT

A device for controlling the flow of liquid to a catheter. Two end caps support a capillary tube that provides continuous flow of liquid from one end cap to the other. A flexible, resilient sleeve is connected at its ends to said end caps and surrounds said capillary tube. Said sleeve, when pulled away from said capillary tube, provides an alternate high flow volume flow from one end cap to the other outside of the tube.

2 Claims, 1 Drawing Sheet

FLUSH CONTROL DEVICE

This invention relates to a device for controlling the flow of liquid, and more particularly, this invention relates to a device for providing a metered low rate of flow through a capillary tube with provision for bypassing the capillary tube to provide a fast flush of liquid.

In the monitoring of blood pressure in the patient, a catheter is inserted in the patient's blood vessel. The catheter is connected to a blood pressure transducer by plastic tubing. A supply of saline solution is connected to the plastic tubing through a flow control device. The flow control device provides a steady drip of liquid through a capillary tube into the catheter to keep the tube from clogging with clotted blood. The flow control device also provides for a fast flush around the capillary. The fast flush is useful in priming the system and in rapidly clearing out any blood backed up into the system during blood withdrawal procedures and the like.

It is important to keep the system filled with a saline solution that is free of air bubbles, for it is through the saline solution that the pressure from the blood vessel is transmitted to the transducer and continuously monitored. The prior art devices include a pair of opposed end caps, a capillary tube between the end caps and a flexible, resilient sleeve surrounding the capillary tube. When the sleeve is deformed as by pulling it away from the capillary tube, liquid can bypass the capillary tube, thereby providing a flush mode of operation. In many prior art embodiments of the invention the capillary has an annular ring intermediate its ends. The flexible sleeve engages the annular ring thus creating a dam or valve normally preventing the flush flow of liquid around the capillary. When the sleeve is pulled away from the dam, the flush flow occurs.

The prior art devices have their problems. Those which have an annular ring surrounding the capillary tube to form a dam create a substantial surface area of resilient tubing which is in the path of the saline solution to the transducer. Thus, the pressure emanating from the blood vessel and transmitted to the saline solution will be damped by the resilient sleeve. Another problem with the prior art is that the flush device has too many parts and/or the parts are of a complex shape, all of which contribute to the cost of making the parts and the labor for assembling the parts.

An objective of the present invention has been to reduce to its simplest form the structure of the flow control device while at the same time improving the operational characteristics of the device over at least some of the prior art devices.

This objective of the invention has been attained by reducing the number of parts in the assembly to four, namely, two end caps, a capillary tube and a resilient sleeve. The two end caps are solvently joined together providing a rigid casing for the device. The capillary tube is long and seats within the cylindrical recesses in the end caps. This tube increases the rigidity and overall strength of the device. Finally, the end caps have large cylindrical recesses which receive the cylindrical ends of the resilient sleeve, thereby adding further to the ruggedness of the device.

The capillary tube has no annular ring to form a dam. Rather, the resilient sleeve has two axially-extending channels of minimal surface area, the channels being separated by a dam which normally contacts the capillary tube. A pull tab positioned immediately adjacent the dam is provided for pulling on the resilient sleeve to lift the dam away from the surface of the capillary tube, thereby permitting the liquid to pass at a high rate over the outer surface of the capillary tube thereby bypassing the capillary tube.

The several features of the invention will become more readily apparent from the following detailed description taken in conjunction with the accompanying drawings in which.

Figure 3:
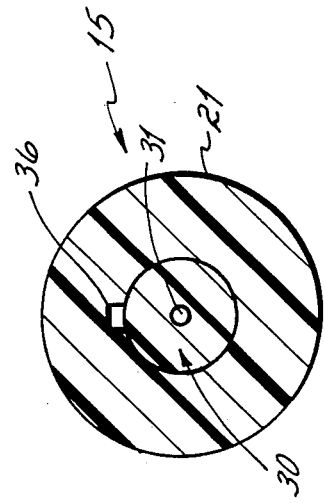
FIG. 3 is a cross-sectional view taken along lines 3—3 of FIG. 1.
Figure 1:
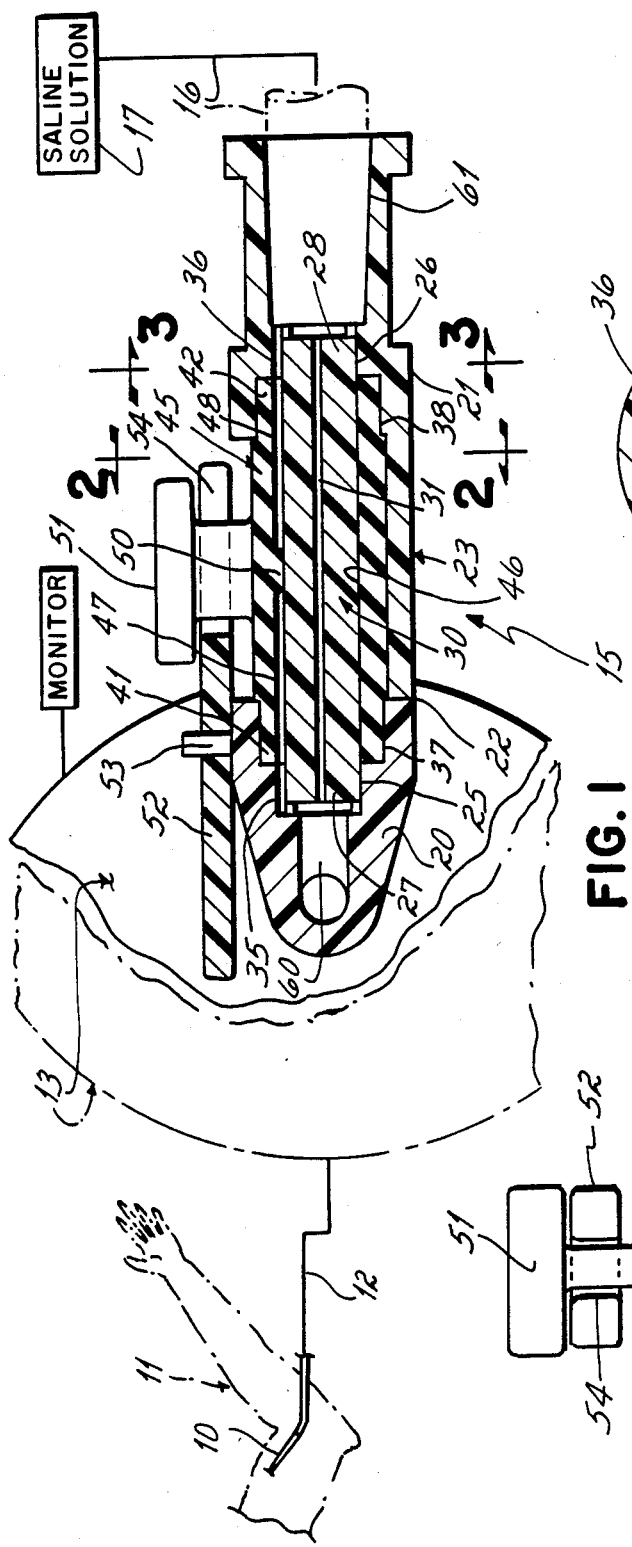
FIG. 1 is a top plan view partly in section showing the flow control device mounted in association with a transducer dome, with the rest of the system being illustrated diagrammatically.
Figure 2:
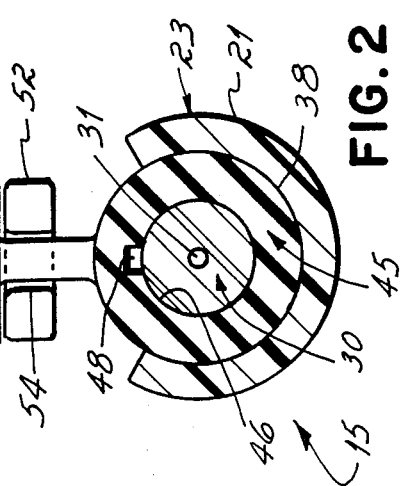
FIG. 2 is a cross-sectional view taken along lines 2—2 of FIG. 1.

As shown in FIG. 1, a capillary 10 is inserted into the blood vessel in the arm 11 of a patient. Flexible tubing 12 connects the catheter to a transducer dome 13. A flow control device 15 is mounted on the transducer dome. The flow control device 15 is connected by flexible tubing 16 to a supply of saline solution 17. The saline solution, coupled with the flexible tube 12, provides a liquid column by which the variations in the pressure of the blood in the blood vessel are transmitted to the transducer dome. The transducer dome is connected in a conventional manner to a transducer which is in turn electrically connected to a monitor by which the blood pressure of the patient is continuously monitored.

The flow control device has an end cap 20 which may be integrally mounted with the transducer dome. It is to be understood that the transducer dome and the end cap 20 could be separate elements connected by flexible tubing, for example. An opposed end cap 21 is joined by a solvent along a joint 22 to end cap 20 to provide a casing 23 for the flow control device. The end caps have cylindrical recesses 25 and 26. Those recesses receive the ends 27 and 28 of a capillary tube 30. The capillary tube 30 has a capillary bore 31 through which liquid continuously passes from a supply 17 to the catheter 10. Each recess 25 and 26 has a channel 35, 36 through which liquid can flow from the end cap around the end portion 27, 28 of the capillary tube.

The end caps have larger cylindrical recesses 37, 38 which receive the ends 41 and 42 of a resilient sleeve 45. The sleeve ends are press-fitted into the end cap recesses to provide a liquid-tight fit. The internal surface of the sleeve 45, indicated at 46, is for the most part a cylinder lying tightly against the outer surface of the capillary tube. The internal surface 46 has axially-extending channels 47 and 48 which are in alignment with the channels 35 and 36 in the end caps so that the channels form passageways for the flow of liquid from one end cap to the other. The internal surface of the sleeve has a dam 50 located between the channels 47 and 48. The dam lies snugly against the surface of the capillary tube thereby blocking the flow of liquid from one channel 48 to the other channel 47. The resilient sleeve has a pull tab 51 projecting radially from the outer surface of the sleeve and overlying the dam 50. When the pull tab is pulled, it lifts the dam 50 off the surface of the capillary tube thereby permitting a flush flow of liquid over the surface of the capillary and into the catheter. For convenience, a lever 52 is pivotally mounted at 53 on the end cap 20. The lever has a forked end 54 which engages the pull tab. When the lever 52 is squeezed against the end cap 20, it will lift the pull tab and hence pull the dam away from the surface of the capillary tube.

The end caps 20, 21 of course have bores 60 and 61, the bore 61 being connected to the supply 17 of the solution and the bore 60 being connected directly to the transducer dome.

In the operation of the invention, liquid from the bag 17 applying a pressure of about 6 psi maximum causes liquid to pass slowly through the capillary bore 31 to the patient. This liquid flow is just sufficient to prevent the blood around the catheter from coagulating and blocking the transmission of information to the monitor. To prime the system, the resilient sleeve 45 with dam 50 is pulled away from the capillary tube by pulling on the pull tab 51 thereby allowing liquid to flow around the capillary tube through the transducer dome to the catheter. As can be seen, there are a minimum of corners and the like in the system and hence the flushing will quickly chase all of the bubbles from the system. When the system is flushed and a prime of saline solution fills all of the elements, the catheter can be inserted into the arm of the patient, whereupon the continuous monitoring of blood pressure takes place.

From the above disclosure of the general principles of the present invention and the preceding detailed description of a preferred embodiment, those skilled in the art will readily comprehend the various modifications to which the present invention is susceptible. Therefore, we desire to be limited only by the scope of the following claims and equivalents thereof:

Having described our invention, we claim:

1. A device for controlling the flow of liquid to a catheter in a blood vessel comprising:
    two axially-aligned end caps that are joined together to form a casing, said end caps having liquid passages therein,
    an elongated capillary tube having opposing ends supported in respective end caps,
    and a flexible resilient sleeve surrounding said capillary tube, said sleeve having its ends fitted into said end caps and in liquid communication therewith,
    said sleeve having an axially-extending groove interrupted by a central dam which is in engagement with said capillary tube,
    said sleeve being in contact with said capillary tube everywhere along the length of said sleeve except for said groove,
    said sleeve having a pull tab for pulling said dam away from said tube,
    whereby liquid normally flows slowly from one end cap through said capillary to said other end cap and when said dam is pulled away, said liquid flows rapidly along said axially-extending groove from one end cap to the other.
2. A flow controlling device of claim 1 in which
    each said end cap has a large cylindrical recess which receives an end of said sleeve, and a small cylindrical recess which receives an end of said capillary tube projecting beyond said sleeve,
    each end cap having, in its small recess, an axial groove aligned with the axially-extending groove in said sleeve whereby to form a high volume flow path, interrupted only by said dam, from one end cap to the other.

* * * * *